(12) United States Patent
Wu et al.

(10) Patent No.: US 10,392,490 B2
(45) Date of Patent: Aug. 27, 2019

(54) POLYPROPYLENE/INORGANIC PARTICLE BLEND COMPOSITION FOR PVC-FREE WEAR LAYER IN RESILIENT FLOORING

(71) Applicant: Dow Global Technologies LLC, Midland, MI (US)

(72) Inventors: Xiaosong Wu, Freeport, TX (US); Ron Weeks, Freeport, TX (US); Rennisha Wickham, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/738,669

(22) PCT Filed: Jun. 21, 2016

(86) PCT No.: PCT/US2016/038517
§ 371 (c)(1),
(2) Date: Dec. 21, 2017

(87) PCT Pub. No.: WO2017/003762
PCT Pub. Date: Jan. 5, 2017

(65) Prior Publication Data
US 2018/0194919 A1 Jul. 12, 2018

Related U.S. Application Data

(60) Provisional application No. 62/186,539, filed on Jun. 30, 2015.

(51) Int. Cl.
*C08L 23/16* (2006.01)
*C08F 210/06* (2006.01)
*C08K 3/013* (2018.01)
*C08K 3/36* (2006.01)
*C09D 123/14* (2006.01)
*C08L 23/14* (2006.01)
(Continued)

(52) U.S. Cl.
CPC .............. *C08K 3/013* (2018.01); *C08K 3/36* (2013.01); *C08L 23/14* (2013.01); *C08L 23/16* (2013.01); *C09D 123/14* (2013.01); *C08F 10/06* (2013.01); *C08F 110/06* (2013.01); *C08F 210/02* (2013.01); *C08F 210/06* (2013.01); *C08F 2500/08* (2013.01); *C08F 2500/12* (2013.01); *C08K 2201/006* (2013.01); *C08L 2201/10* (2013.01); *C08L 2312/00* (2013.01); *C08L 2666/72* (2013.01); *E04F 15/105* (2013.01); *G01N 25/4866* (2013.01)

(58) Field of Classification Search
None
See application file for complete search history.

(56) References Cited

U.S. PATENT DOCUMENTS 5,391,612 A 2/1995 Johnson
6,103,657 A 8/2000 Murray
(Continued)

FOREIGN PATENT DOCUMENTS

WO 2013/034618 A1 3/2013

*Primary Examiner* — Richard A Huhn
(74) *Attorney, Agent, or Firm* — Husch Blackwell LLP (57) ABSTRACT

Embodiments of this invention relate to a composition composed of at least (A) a propylene-based polymer, and (B) a filler dispersed within the propylene-based polymer, which can be used as a wear layer on a resilient flooring or other substrate, among other uses.

17 Claims, 1 Drawing Sheet

(51) Int. Cl.
  *C08F 110/06* (2006.01)
  *C08F 10/06* (2006.01)
  *C08F 210/02* (2006.01)
  *E04F 15/10* (2006.01)
  *G01N 25/48* (2006.01)

(56) References Cited

U.S. PATENT DOCUMENTS

| | | |
|---|---|---|
| 6,218,001 B1 | 4/2001 | Chen et al. |
| 6,320,005 B1 | 11/2001 | Murray |
| 6,620,888 B2 | 9/2003 | Resconi et al. |
| 6,706,829 B2 | 3/2004 | Boussie et al. |
| 6,953,764 B2 | 10/2005 | Frazier et al. |
| 6,960,635 B2 | 11/2005 | Stevens et al. |
| 7,355,089 B2 | 4/2008 | Chang et al. |
| 7,608,668 B2 | 10/2009 | LiPiShan et al. |
| 7,833,611 B2 | 11/2010 | Phan et al. |
| 7,858,706 B2 | 12/2010 | Arriola et al. |
| 7,951,882 B2 | 5/2011 | Arriola et al. |
| 8,076,147 B2 | 12/2011 | Van Damme et al. |
| 8,318,896 B2 | 11/2012 | Winniford et al. |
| 8,476,393 B2 | 7/2013 | LiPiShan et al. |
| 8,592,501 B2 | 11/2013 | Phan et al. |
| 8,691,916 B2 | 4/2014 | Wu et al. |
| 2008/0311812 A1 | 12/2008 | Arriola et al. |
| 2009/0105397 A1* | 4/2009 | Van Riel ............... C08F 297/08 524/505 |
| 2012/0276348 A1 | 11/2012 | Clausi et al. |
| 2014/0138021 A1 | 5/2014 | Schlisner |
| 2015/0064434 A1 | 3/2015 | Bastin et al. |

\* cited by examiner

POLYPROPYLENE/INORGANIC PARTICLE BLEND COMPOSITION FOR PVC-FREE WEAR LAYER IN RESILIENT FLOORING

REFERENCE TO RELATED APPLICATIONS

The present application claims the benefit of U.S. Provisional Application No. 62/186,539, filed on Jun. 30, 2015, and incorporated herein by reference.

FIELD OF THE INVENTION

Embodiments of this invention relate to a composition composed of at least (A) a propylene-based polymer, and (B) a filler dispersed within the propylene-based polymer, which can be used as a wear layer on a resilient flooring or other substrate, articles made from the composition, and methods of producing the composition and articles.

BACKGROUND OF THE INVENTION

Luxury vinyl tile (LVT) is one of the fastest growing segments in the flooring market taking share from laminates, true hardwood and other vinyl segments. These tiles and planks are typically composed of a highly filled base layer situated beneath a decorative film, which is in turn covered by a clear wear layer. Key performance requirements of materials for LVT wear layers include scratch/abrasion resistance, optical clarity, flexibility, correct coefficient of friction (COF), and dimensional stability.

The most common polymer used in LVT wear layers is plasticized polyvinyl chloride (P-PVC). However, growing environmental concerns centered on plasticizer emissions (both during manufacture and end-use) and the recyclability and reprocessing issues of P-PVC have urged manufacturers to look for replacement materials for P-PVC. Another environmental issue with PVC LVTs is that when the material burns, hazardous halogen-containing products of combustion, such as hydrogen chloride, can be formed.

Polypropylene/inorganic particle-based blend compositions have been disclosed for various industrial applications including resilient flooring. However, such materials fail to provide a good balance of the essential properties for a wear layer, including scratch/abrasion resistance, reduced migrating moiety, optical clarity and adhesion properties.

It would, therefore, be desirable to provide a material that can be used for a wear layer in LVT resilient flooring coverings, which is halogen-free to eliminate the potential for formation of hydrogen chloride when the floor covering is burned, does not contain a liquid plasticizer, is recyclable, and provides a PVC-free material that has an improved balance of properties including reduced migrating moieties, and high scratch/abrasion resistance, optical clarity and adhesion properties. These needs and others have been met by the following invention.

SUMMARY OF THE INVENTION

In embodiments, the invention provides a composition comprising at least the following:

A) At least 50 wt %, based on the total weight of the composition, of a propylene-based polymer that has a % crystallinity by differential scanning calorimetry (DSC) of greater than, or equal to, 25% and a MFR from 0.5 to 30.0 g/10 min (230° C./2.16 kg); and B) From 0.5 to 10.0 wt % of a filler, based on the total weight of the composition.

In an embodiment, the composition comprises:

A. From 80 to 99.5 wt % of a propylene-based polymer having a MFR from 0.5 to 30 g/10 min (2.16 kg @ 230° C.), less than 10 wt % ethylene monomers, a density of 0.888 to 0.910 g/cm$^3$, a unimodal molecular weight distribution, and a MWD of less than 3; and B. From 0.5 to 10% of an inorganic micro- or nano-particle filler.

The disclosed blends possess excellent abrasion resistance, good scratch/mar resistance, and good optical clarity.

In another aspect, the invention provides a crosslinked composition formed from the composition as disclosed herein.

In another aspect, the invention provides an article comprising at least one component formed from the composition as disclosed herein.

In yet another aspect, the invention provides a method of providing a crosslinked material comprising a filler dispersed within a crosslinked polypropylene-based.

DETAILED DESCRIPTION OF THE INVENTION

Various embodiments of the present invention relate to a composition comprising at least (A) a propylene-based polymer, and (B) a filler dispersed within the propylene-based polymer. Additionally, certain embodiments concern crosslinked compositions and articles of manufacture employing such polymer materials, and methods for preparing the polymer materials. It was surprisingly found that the addition of micro-sized or nano-sized inorganic particles of a filler component to a propylene-based polymer provides a composition having both a high level of scratch/abrasion resistance while maintaining a surprisingly low level of internal haze.

Propylene-Based Polymers

In one embodiment, the propylene-based polymer of component A is a propylene/α-olefin interpolymer. In a further embodiment, the propylene/α-olefin interpolymer is a propylene/α-olefin copolymer.

In one embodiment, the propylene-based polymer of component A is a propylene/ethylene interpolymer. In a further embodiment, the propylene/ethylene interpolymer is a propylene/ethylene copolymer.

In some embodiments, the propylene-based polymer comprises, in polymerized form, greater than (>) 50, or greater than or equal to (≥) 80, or greater than or equal to 85, or greater than or equal to 90, wt % propylene monomer units, based on the total weight of the polymer.

In some embodiments, the propylene-based polymer is a propylene/α-olefin interpolymer (e.g., plastomer or elastomer). Such propylene/α-olefin interpolymers include reactor grade copolymers of propylene having a heat of fusion less than about 100 J/g and MWD<3.5. These polypropylene/α-olefin interpolymers, as plastomers, generally have a heat of fusion less than about 100 J/g, and a weight percent ethylene or other α-olefin in the range of 3 to 15 wt %. These polypropylene/α-olefin interpolymers, as elastomers, generally have a heat of fusion less than about 40 J/g and a weight percent ethylene or other α-olefin in the range of 10 to 15 wt % ethylene.

In some embodiments, the propylene-based polymer is a random propylene/α-olefin interpolymer. A random propylene/α-olefin interpolymer is an interpolymer in which the monomers are randomly distributed across the polymer chain.

Examples of α-olefin comonomers suitable for use in the propylene-based polymer include, but are not limited to, $C_{2-20}$ (i.e., having 2 to 20 carbon atoms) linear, branched, or cyclic α-olefins. Examples of $C_{2-20}$ α-olefins include ethylene (considered an α-olefin for purposes of this invention), 1-butene, 1-pentene, 1-hexene, 1-octene, 1-decene, 1-dodecene, 1-tetradecene, 1-hexadecene, and 1-octadecene. In embodiments, the α-olefins can also have a cyclic structure such as cyclohexane or cyclopentane, resulting in an α-olefin such as 3-cyclohexyl-1-propene (allyl cyclohexane) and vinyl cyclohexane. Illustrative propylene/α-olefin interpolymers include propylene/ethylene, propylene/1-butene copolymers, propylene/1-hexene copolymers, propylene/1-octene copolymers, or combinations of two or more thereof.

Commercial examples of propylene-based polymers suitable for use herein include, but are not limited to, random propylene/ethylene interpolymer plastomers and elastomers such as VERSIFY™ polymers (The Dow Chemical Company), VISTAMAXX™ polymers (ExxonMobil Chemical Co.), and LICOCENE™ polymers (Clariant) and Ziegler-Natta catalyzed non-random propylene copolymers such as Braskem RCP 6D83K and DS6D81, Exxon Mobil PP 9122 and PP 9513. Other examples include, amorphous poly (α-olefins) such as EASTOFLEX™ polymers (Eastman Chemical Co.), REXTAC™ polymers (Hunstman), and VESTOPLAST™ polymers (Degussa).

In some embodiments, the propylene-based polymer has a molecular weight distribution (MWD) from 1.0 to 3.0, or from 1.5 to 2.5. In other embodiments, the propylene-based polymer has an MWD of 2.0 to 4.0, or 2.0 to 3.5, or 2.5 to 3.0.

In some embodiments, the propylene-based polymer has a narrow molecular weight distribution (MWD) and narrow Comonomer Composition Distribution Breadth ("CCDB") of propylene. In embodiments, the propylene-based polymer has a Comonomer Composition Distribution Breadth ("CCDB") of less than 2, or less than 1.5, or less than 1, as determined according to the HTLC test method as described herein.

In some embodiments, the propylene-based polymer has a percent (%) crystallinity of greater than or equal to (≥) 25%, or greater than or equal to 35%, or greater than or equal to 40%; to less than or equal to 60%, or less than or equal to 55%, or less than or equal to 50%, or less than or equal to 46% as measured by differential scanning calorimetry ("DSC"). In embodiments, the propylene-based polymer has a % crystallinity from 25 to 60%, or from 30 to 55%, or from 35 to 55%; or from 40 to 55%, or from 40 to 50%.

In some embodiments, the propylene-based polymer has a density greater than, or equal to, 0.888 g/cm³, or greater than, or equal to, 0.892 g/cm³, or greater than, or equal to, 0.902 g/cm³, to less than, or equal to, 0.910 g/cm³, as determined according to ASTM D-792. In embodiments, the propylene-based polymer has a density ranging from 0.888 to 0.910 g/cc, or from 0.892 to 0.902 g/cm³.

In some embodiments, the propylene-based polymer has a melt flow rate (MFR), of greater than or equal to 0.5, or greater than or equal to 1, or greater than or equal to 1.5, or greater than or equal to 2.0, to less than or equal to 30, or less than or equal to 25, or less than or equal to 20, g/10 min, as measured by ASTM D1238 at 230° C./2.16 kg. In embodiments, the propylene-based polymer has a MFR of 0.5 to 30, or 1.0 to 25, or 2.0 to 20, g/10 min (230° C./2.16 kg).

In some embodiments, the propylene-based polymer has a melt flow rate (MFR) of greater than or equal to 3.0, or greater than or equal to 4.0, or greater than or equal to 5.0, or greater than or equal to 7.0, to less than or equal to 30, or less than or equal to 25, or less than or equal to 20, or less than or equal to 15, g/10 min, as measured by ASTM D1238 at 230° C./2.16 kg. In embodiments, the propylene-based polymer has a MFR of 3.0 to 30, or 5.0 to 25, or 5.0 to 20, or 5.0 to 15, g/10 min (230° C./2.16 kg).

In some embodiments, the propylene-based polymer has a melting point of at least 100° C., or at least 105° C., or at least 110° C., and less than 150° C., or less than 140° C., or less than 130° C. In embodiments, the propylene-based polymer has a melting point from 100 to 150° C.

In various embodiments, the propylene-based polymer (component A) can be a combination of two or more of the described propylene-based polymers. For example, a propylene-based polymer having one or more properties outside a desired range may be combined with a second propylene-based polymer so that the blend of the two polymers has the desired properties.

In various embodiments, the composition comprises the propylene-based polymer (Component A) in an amount greater than, or equal to 80 wt %, or greater than, or equal to 85 wt %, or greater than, or equal to 90 wt %, to less than, or equal to, 99.5 wt %, or less than or equal to 98 wt %, or less than, or equal to, 95 wt %, based on the total weight of the composition. In various embodiments, the composition comprises the propylene-based polymer (Component A) in an amount of 80 to 99.5 wt %, or 90 to 99.5 wt %, or 85 to 95 wt %, based on the total weight of the composition.

Preparation of Propylene-Based Polymers

Production processes used for preparing propylene-based polymers are wide, varied, and known in the art. Any conventional or hereafter discovered production process for producing propylene-based polymers having the described properties may be employed for preparing the elastomers described herein. The propylene-based polymer can be made using a variety of catalysts, including metallocene or other single site catalysts, and Ziegler-Natta catalysts.

In some embodiments, the propylene-based polymers are made using advanced catalyst technology, as described, for example, in U.S. Pat. No. 8,691,916.

Suitable catalysts and catalyst precursors for use in the present invention include metal complexes such as disclosed in WO2005/090426, in particular, those disclosed starting on page 20, line 30, through page 53, line 20. Suitable catalysts are also disclosed in U.S. Pat. Nos. 7,608,668, 7,858,706, 7,951,882, 7,355,089, or WO 2009/012215.

Particularly preferred catalysts are those of the following formula:

where each $R^{20}$ is, independently, an aromatic or inertly substituted aromatic group containing from 5 to 20 atoms not counting hydrogen, or a polyvalent derivative thereof; $T^3$ is a hydrocarbylene or silane group having from 1 to 20 atoms not counting hydrogen, or an inertly substituted derivative thereof; $M^3$ is a Group 4 metal, preferably zirconium or hafnium; G is an anionic, neutral or dianionic ligand group; preferably a halide, hydrocarbyl or dihydrocarbylamide group having up to 20 atoms not counting hydrogen; g is a number from 1 to 5 indicating the number of such G groups; and bonds and electron donative interactions are represented by lines and arrows respectively.

Preferably, such complexes correspond to the formula:

wherein: $T^3$ is a divalent bridging group of from 2 to 20 atoms not counting hydrogen, preferably a substituted or unsubstituted, $C_{3-6}$ alkylene group; each $Ar^2$, independently, in each occurrence, is an arylene or an alkyl- or aryl-substituted arylene group of from 6 to 20 atoms not counting hydrogen; $M^3$ is a Group 4 metal, preferably hafnium or zirconium; G independently each occurrence is an anionic, neutral or dianionic ligand group; g is a number from 1 to 5 indicating the number of such X groups; and electron donative interactions are represented by arrows.

Preferred examples of metal complexes of foregoing formula include the following compounds:

where M3 is Hf or Zr, each $Ar^4$ is, independently, $C_{6-20}$ aryl or inertly substituted derivatives thereof, especially 3,5-di(isopropyl)phenyl, 3,5-di(isobutyl)phenyl, dibenzo-1H-pyrrole-1-yl, or anthracen-5-yl, and $T^4$ comprises a $C_{3-6}$ alkylene group, a $C_{3-6}$ cycloalkylene group, or an inertly substituted derivative thereof, $R^{21}$, independently, in each occurrence, is hydrogen, halo, hydrocarbyl, trihydrocarbylsilyl, or trihydrocarbylsilylhydrocarbyl of up to 50 atoms not counting hydrogen; and G, independently, in each occurrence, is halo or a hydrocarbyl or trihydrocarbyl-silyl group of up to 20 atoms not counting hydrogen, or two G groups together are a divalent derivative of the foregoing hydrocarbyl or trihydrocarbylsilyl groups.

Especially preferred are compounds of the formula:

wherein each $Ar^4$ is 3,5-di(isopropyl)phenyl, 3,5-di(isobutyl)-phenyl, dibenzo-1H-pyrrole-1-yl, or anthracen-5-yl, $R^{21}$ is hydrogen, halo, or $C_{1-4}$ alkyl, especially methyl, $T^4$ is propan-1,3-diyl or butan-1,4-diyl, and G is chloro, methyl or benzyl.

Other suitable metal complexes are those of the formula:

The foregoing polyvalent Lewis base complexes are conveniently prepared by standard metallation and ligand exchange procedures involving a source of the Group 4 metal and the neutral polyfunctional ligand source. In addition, the complexes may also be prepared by means of an amide elimination and hydrocarbylation process starting from the corresponding Group 4 metal tetraamide and a hydrocarbylating agent, such as trimethylaluminum. Other techniques may be used as well. These complexes are known from the disclosures of, among others, U.S. Pat. Nos. 6,320,005, 6,103,657, 6,953,764 and International Publication Nos. WO 2002/038628 and WO 2003/040195.

The propylene-based polymers can be made using gas phase, slurry or solution processes as is commonly known in the art.

The propylene-based polymer (component A) may comprise a blend of two or more materials which each comprise a propylene-based polymer as described herein.

Fillers (Component B)

In some embodiments, the composition comprises at least one inorganic filler (Component B). In embodiments, the inorganic filler (Component B) is included in the composition to improve the hardness and scratch and abrasion resistance of coatings or other layers (e.g., wear layers) prepared from the composition.

In some embodiments, the amount, size and type of the filler particles (Component B) are selected such that the composition applied as a layer (e.g., a wear layer) has a high level of contact clarity.

In some embodiments, a sufficient amount of the filler (Component B) is included in the composition to provide a surface covering (e.g., a wear layer) with a desired level of wear resistance which will not interfere with contact clarity of the layer. Wear resistance can be determined, for example, by a Taber abrasion test, a Gardener Scrubber test, a walk test, and the like. In embodiments, the concentration of the filler (Component B) in the composition is sufficient to provide a layer (e.g., wear layer) having a thickness of 10 to 60 mils with a scratch depth less than 1 micron and an internal haze of less than 40%.

In various embodiments, the composition comprises the filler (Component B) in an amount greater than or equal to 0.5 wt %, or greater than or equal to 1 wt %, or greater than or equal to 1.5 wt %, to less than or equal to 10 wt %, or less than or equal to 8 wt %, or less than or equal to 5 wt %, or less than or equal to 4 wt %, or less than or equal to 3 wt %, or less than or equal to 2 wt %, based on the total weight of the composition. In embodiments, the composition comprises the filler (Component B) in an amount of 0.5 to 5, or 0.5 to 4, or 0.5 to 3, or 0.5 to 2, or 1 to 2, wt %, based on the total weight of the composition.

In some embodiments, the particles are in a granular or powdered form. In embodiments, the particles can be shaped as spherical, granular, platelets or rod like agglomerations.

In some embodiments, the size of the particles is such that the particles either minimally or do not scatter light at angles greater than 2.5°, which can increase the internal haze of the material.

In some embodiments, the filler comprises particles with an average surface area per gram of less than 230 $m^2/g$, or less than 190 $m^2/g$, or less than to 150 $m^2/g$, or less than 100 $m^2/g$, or less than 50 $m^2/g$, or less than 25 $m^2/g$, or less than 10 $m^2/g$. In embodiments, the filler particles have a surface area of 5 to 10 $m^2/g$.

In some embodiments, the filler comprises particles with a specific surface area per gram of less than 230 $m^2/g$, or less than 220 $m^2/g$, or less than to 210 $m^2/g$.

In some embodiments, the filler particles have a pH of 3 or greater, or 4 or greater, up to 12, or up to 10, or up to 8, or up to 6, or up to 5.5, or up to 5. In embodiments, the filler particles have a pH of 3 to 12, or 3 to 6, or a pH of 4 to 5.5.

Suitable fillers include, but are not limited to, silicon dioxide (silica, $SiO_2$), aluminum oxide (alumina, $Al_2O_3$), titanium oxide (titania, $TiO_2$), silicon carbide (SiC), glass particles, glass beads, plastic grits, quartz, coal fly ash, calcium carbonate, barium sulfate, carbon black, metal oxides, inorganic material, natural material, alumina trihydrate, alumina silicate, magnesium hydroxide, bauxite, talc, mica, barite, kaolin, silica, post-consumer glass, post-industrial glass, synthetic and natural fiber, or any combination thereof. In embodiments, the filler is a hydrophobic, fumed silica.

Such fillers are known in the art and commercially available. Examples of commercially available fillers include AEROSIL hydrophobic fumed silicas available from Evonik Industries AG, for example, AEROSIL R7200 and AEROSIL R9200 fumed silicas, and Minex alumina silicates, for example Minex 12.

In some embodiments, the filler is a thermally conductive filler. In a further embodiment, the thermally conductive filler is a single filler or a combination of two or more fillers that differ in at least one property, such as particle shape, average particle size, particle size distribution, and type of filler.

In some embodiments, the filler can be melt-mixed in a propylene-based polymer to make a filler-containing masterbatch. In embodiments, the same propylene-based polymer is used for the Component A as the propylene-based polymer used to prepare the filler masterbatch. In embodiments, different propylene-based polymers are used for the Component A polymer and the filler masterbatch. Use of the same propylene-based polymer for both the Component A polymer and the filler masterbatch promotes compatibility and a better interface between the two components. In embodiments, the filler is combined with a random propylene-based copolymer to prepare a masterbatch.

The filler loading in the masterbatch phase can be greater, or equal to, 10 wt %, or greater, or equal to 30 wt %, or greater than, or equal to 40 wt %, up to 90 wt % or less, or up to 85 wt % or less, or up to 80 wt % or less. In embodiments, the masterbatch can have a filler loading of 20 wt % to 90 wt %, or 30 wt % to 85 wt %, or 40 wt % to 80 wt %.

Additives

In some embodiments, the composition can optionally include one or more compatible additives. In embodiments, the composition includes one or more additives in an amount of 0.1 to 5 wt %, based on the total weight of the composition.

Suitable additives include, but are not limited to, crosslinking agents, antioxidants, suspension aids, process oils, plasticizers, lubricants, viscosity control agents, slip agents, anti-blocking agents, tackifiers, coupling agents, processing aids, ultraviolet (UV) absorbers or stabilizers, antimicrobial agents, anti-static agents, colorants or pigments, and combinations thereof. Such additives can be employed in a desired amount to achieve their desired effect.

Examples of suitable antioxidants include, but are not limited to, hindered phenols, bisphenols, and thiobisphenols, and substituted hydroquinones. Examples of commercially available antioxidants include IRGANOX™ 1010 and IRGAFOX™ 168, available from Ciba Specialty Chemicals; IRGANOX™ 1076, available from Ciba-Geigy Corp.

Examples of processing aids include, but are not limited to, waxes (e.g. polyethylene waxes, vegetable waxes, petroleum waxes), metal salts of carboxylic acids (e.g., zinc stearate, calcium stearate, etc.), fatty acids (e.g., stearic acid, oleic acid, erucic acid, etc.), fatty amides such (e.g., stearamide, etc.), polymers of ethylene oxide, copolymers of ethylene oxide and propylene oxide, nonionic surfactants, and polysiloxanes.

Compounding

The compositions can be prepared by conventional or hereafter discovered procedures that provide a mixture of the components as described herein, using equipment such as, but not limited to, mixers for melt blending of the components, and equipment used for continuous mixing procedures including single and twin screw extruders, static mixers, Farrel continuous mixers, Banbury mixers as well as other machines and processes designed to disperse the components in intimate contact.

In some embodiments, the filler or filler-containing masterbatch is melt-mixed with the propylene-based polymer (Component A) using a melt-mixing method. Melt mixing of the filler and the propylene-based polymer can be achieved by conventional or hereafter discovered melt-mixing procedures. For example, melt extrusion or mixing in a HAAKE melt mixer can be employed. In embodiments, the filler (Component B) or filler-containing masterbatch can then be added to the propylene-based polymer (Component A) in an amount determined to provide the desired concentration of filler in the end product composition. Additives, if employed, can be melt-mixed at any time, either in the masterbatch phase, the non-masterbatch phase, or the combined material.

In some embodiments, the composition comprises the propylene-based polymer (Component A) in an amount of 80 to 99.5 wt %, the filler (Component B) in an amount of 0.5 to 10 wt %, and optionally, one or more additives in an amount of 0.1 to 5 wt %, based on the total weight of the composition.

In some embodiments of the composition, the combined wt % of the propylene-based polymer (component A), and the filler (component B) in the composition is greater than or equal to ($\geq$) 95 wt %, or $\geq$98 wt %, or $\geq$99 wt %, based on the total weight of the composition.

In some embodiments, the weight ratio of component A to component B is greater than 20, or greater than 50, or greater than 60, or greater than 80, up to 200.

In some embodiments, the composition has a MFR from 2 to 13 g/10 min., or from 4 to 11 g/10 min. (230° C./2.16 kg).

In some embodiments, the composition has a percent (%) crystallinity of greater than or equal to ($\geq$) 30%, or greater than or equal to 35%, or greater than or equal to 40%; to less than or equal to 75%, or less than or equal to 70%, or less than or equal to 65%, or less than or equal to ($\leq$) 60%, or less than or equal to 55%, as measured by differential scanning calorimetry ("DSC"). In embodiments, the composition has a % crystallinity of 30 to 75%, or 35 to 70%, or 40 to 65%, or 40 to 60%, or 40 to 55%.

In some embodiments, the composition has a scratch depth ($\mu$m) of less than or equal to ($\leq$) 1.00 $\mu$m, or less than or equal to 0.95 $\mu$m, or less than or equal to 0.90 $\mu$m, or less than or equal to 0.85 $\mu$m, as measured on an injection molded plague, using a Krauss Maffei KM 110-390/390 CL injection molder, and has dimensions of 16.5 mm×19 mm×3 mm (4 in×6 in×0.125 in), and is generated at rates of 150 rpm and temperatures of 200° C. using a single mold.

In some embodiments, the composition has a Modulus (Avg-10%), in psi, of greater than or equal to ($\geq$) 3000 psi, or greater than or equal to 3200 psi, or greater than or equal to 3400 psi; In embodiments, the composition has a Modulus (Avg-10%) from 3000 to 6000 psi, or from 3200 to 6000 psi, or from 3400 to 6000 psi.

The compositions may comprise a combination of two or more embodiments described herein.

Articles of Manufacture

In some embodiments, the composition can be used as the top layer or outermost wear layer on a surface of a substrate (e.g., a multilayer substrate) such as, but not limited to, tiles, resilient flooring, slip-resistant flooring, wall paper, countertops, wall coverings, automobile dash boards, automotive coatings, and wall coverings, among others.

In various embodiments, the composition can be combined with other materials to form a wear layer on a laminated substrate (e.g., a floor covering).

Figure 1:
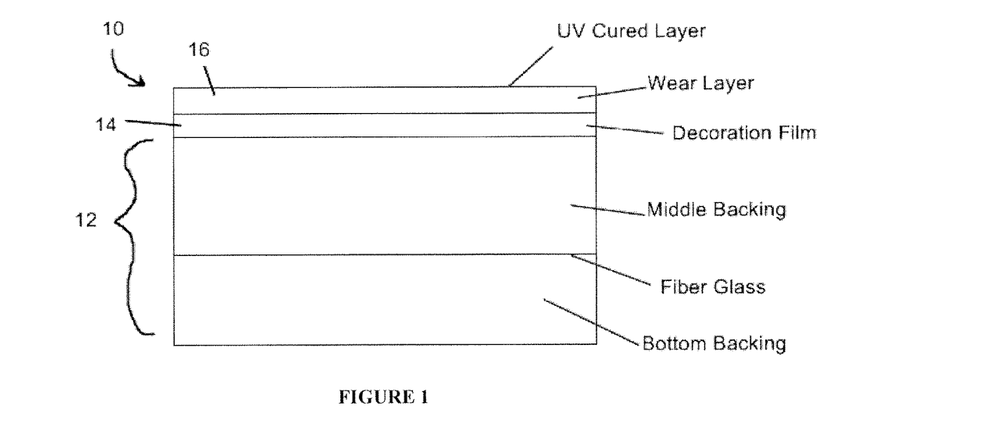
FIG. 1 depicts a multilayer resilient floor tile.

FIG. 1 is a depiction of an example of a multilayer resilient floor tile. In embodiments, the laminated substrate (10) can include a base substrate (12), a décor layer (or printed layer) (14) affixed to a surface of the base substrate (12), and a wear layer (16) comprising the inventive composition overlying and affixed to the surface of the décor (or printed) layer (14). In embodiments, the laminated substrate can include one or more additional material layers. In embodiments, the décor layer (or printed layer) can comprise a gravure print, a digital print, a flexo print, a transfer print, a pad print, a stamping print, a decorative painting, or any combination thereof. In embodiments, the décor layer (or printed layer) comprises a substrate, which in embodiments, comprises one or more polymer films and/or papers. In embodiments, the décor layer (or printed layer) comprises a non-PVC thermoplastic film (e.g., acrylic, polyolefin, ionomer, polyester, etc.). In embodiments, a wear layer comprising the composition of the invention, can be applied to the surface of the décor layer (or printed layer) as a single layer or multiple layer construction, In embodiments, the thickness of a wear layer, can be from 10 to 60 mils, or 15 to 45 mils. The wear layer must not be too thin or a poor stain resistance results, but it must not be too thick so as not to compromise internal haze and/or flexibility.

In embodiments, a layer formed from the composition has a scratch depth value of less than 1 $\mu$m and an internal haze value of less than 40%.

Films, including multi-layer films, may be produced by cast or entering process, including blown film processes.

The inventive compositions may also be processed into an article by any one of a number of conventional techniques and apparatus. Illustrative processes include, but are not limited to, injection molding, extrusion molding, thermoforming, compression molding, rotomolding, slush molding, over molding, insert molding, blow molding, calendering, and other processing techniques that are well known to those skilled in the art.

Articles include, but are not limited to, sheets, molded goods and extruded parts. Additional articles include automotive parts, weather strips, belts, hoses, wire and cable jacketing and insulations, seals, O-rings, tire components, computer parts, building materials, among other applications.

An article may comprise a combination of two or more embodiments described herein.

Definitions

Unless stated to the contrary, implicit from the context, or customary in the art, all parts and percents are based on weight, and all test methods are current as of the filing date of this disclosure.

For purposes of United States patent practice, the contents of any referenced patent, patent application or publication are incorporated by reference in their entirety (or its equivalent US version is so incorporated by reference) especially with respect to the disclosure of synthetic techniques, product and processing designs, polymers, catalysts, definitions (to the extent not inconsistent with any definitions specifically provided in this disclosure), and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, weight percentages, etc., is from 100 to 1,000, then the intent is that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 0.9, 1.1, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the amounts of various components in the inventive composition, and the various characteristics and properties by which these compositions and the optical cable protective components made from these compositions are defined.

"Aspect ratio," as used herein, refers to a ratio of an average value of the longest dimension to the average value of the shortest dimension. With respect to rod or needle shaped particles, aspect ratio refers to a ratio of an average value of the particle length (i.e., the longest dimension) to the average value of the particle width or diameter (i.e., the shortest dimension). With respect to particles that have a plate-like shape, aspect ratio refers to a ratio of an average value of particle width or diameter (i.e., the longest dimension) to the average value of the particle thickness (i.e., the shortest dimension). With respect to spheres, the aspect ratio refers to the ratio between the long and short axes of the particle.

"Composition" and like terms, as used herein, mean a mixture or blend of two or more materials which comprise the composition, as well as reaction products and decomposition products formed from the materials of the composition.

"Comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

"Elastomer" and like terms, as used herein, denote a polymer having viscoelasticity. Generally, elastomers will have lower tensile modulus and higher failure strain relative to other materials, such as thermoplastics.

"Ethylene-based polymer" and like terms, as used herein, refers to a polymer that comprises, in polymerized form, a majority amount of ethylene monomer (based on the weight of the polymer), and optionally may comprise one or more comonomers.

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure), and the term interpolymer as defined hereinafter. Trace amounts of impurities, for example, catalyst residues, may be incorporated into and/or within the polymer.

"Interpolymer" and like terms, as used herein, mean a polymer prepared by the polymerization of at least two different types of monomers. The generic term interpolymer thus includes copolymers (employed to refer to polymers prepared from two different types of monomers), and polymers prepared from more than two different types of monomers (e.g., terpolymers (three different monomer types) and tetrapolymers (four different monomer types)).

"Olefin-based polymer," as used herein, refers to a polymer that comprises, in polymerized form, ≥50 wt % of an olefin (for example, propylene or ethylene), based on the weight of the polymer, and optionally one or more comonomers. Preferably, the olefin-based polymer comprises, in polymerized form, a majority amount of olefin (for example, propylene or ethylene), based on the weight of the polymer, and optionally one or more comonomers.

"Plastomer" and like terms, as used herein, denote a polymer that softens when heated and hardens when cooled, yet remains flexible "Platy," "platelike, and like terms, as used herein, refer to the morphology or shape of a particle as resembling a thin, flat plate or sheet.

"Polymer" and like terms, as used herein, refer to a polymeric compound prepared by polymerizing monomers, whether of the same or a different type. The generic term polymer thus embraces the term "interpolymer" as defined herein. Trace amounts of impurities, such as catalyst residues, can be incorporated into and/or within the polymer.

"Propylene-based polymer," as used herein, refers to a polymer that comprises, in polymerized form, ≥50 wt % of propylene, based on the weight of the polymer, and optionally one or more comonomers. Preferably, the propylene-based polymer comprises, in polymerized form, a majority amount of propylene monomer, based on the weight of the polymer, and optionally one or more comonomers.

"Propylene-based interpolymer", "propylene-based elastomer" and like terms, as used herein, refer to a polymer that comprises, in polymerized form, ≥50 wt % of propylene monomer (based on the total weight of the polymer), and at least one comonomer. Preferably, the propylene-based interpolymer", "propylene-based elastomer" and like terms, comprise, in polymerized form, a majority weight percent (wt %) of propylene monomer (based on the total weight of the polymer), and at least one comonomer.

"Propylene/α-olefin interpolymer," as used herein, refers to an interpolymer that comprises, in polymerized form, ≥50 wt % of propylene monomer (based on the weight of the interpolymer), and at least one α-olefin. Preferably, the propylene/α-olefin interpolymer comprises, in polymerized form, a majority amount of propylene monomer (based on the weight of the interpolymer), and at least one α-olefin.

"Propylene/α-olefin copolymer," as used herein, refers to a copolymer that comprises, in polymerized form, ≥50 wt % of propylene monomer (based on the weight of the copolymer), and an α-olefin, as the only two monomer types. Preferably, the propylene/α-olefin copolymer comprises, in polymerized form, a majority amount of propylene monomer (based on the weight of the copolymer), and at least one α-olefin, as the only two monomer types.

"Propylene/ethylene copolymer," as used herein, refers to an copolymer that comprises, in polymerized form, ≥50 wt % of propylene monomer (based on the weight of the copolymer), and ethylene, as the only two monomer types. Preferably, the propylene/ethylene copolymer comprises, in polymerized form, a majority weight percent (wt %) (i.e., >50 wt %) of propylene monomer (based on the weight of the copolymer), and ethylene, as the only two monomer types.

"Propylene random interpolymer," "Propylene random copolymer," and like terms, as used herein, refer to a polymer that comprises, in polymerized form, ≥50 wt % of propylene monomer (based on the weight of the polymer), and at least one comonomer randomly distributed across the polymer chains. Preferably, the propylene random interpolymer," "propylene random copolymer," and like terms, comprise, in polymerized form, a majority weight percent (wt %) of propylene monomer (based on the weight of the polymer), and at least one comonomer randomly distributed across the polymer chains.

Test Methods

Density, in g/cm$^3$, of polymers as provided herein, is determined according to ASTM International ("ASTM") method D792. Each sample was compression molded, as discussed below for the flexural modulus test. Isopropyl alcohol, at 23° C., was used for sample immersion. An average of the three (3) measurements was taken.

Total (Overall) Haze and Internal Haze is measured according to using a Standard Test Method for Haze and Luminous Transmittance of Transparent Plastics, ASTM D1003-07, on cast films or injection molded plaques (see the experimental section below). The percentage of luminous transmission which is passing through the specimen deviates from the incident beam by forward scattering. For the purpose of this method only luminous flux deviating more than 2.5° on the average is considered haze. Five samples were prepared across—surface area approximately 6"×6". The samples are chosen randomly across both axes to provide a more homogenous sample selection. The samples are placed in a ring fixture to remove surface wrinkles. Internal haze sample specimens were coated with mineral oil, using a cotton swab on both sides, to separate the measured total haze into its bulk (internal haze) and surface (external haze) components. After running a calibrated sample, each specimen is held across the transmitter, and the results are recorded. Specimen thickness is measured as well, taking the average of three readings using a flat headed digital micrometer.

Melt flow rates (MFR), in g/10 minutes, as provided herein, are determined according to ASTM D1238 (at 230° C./2.16 kg).

Melt Index ($I_2$) is determined according to ASTM method D1238. Unless otherwise noted, melt index ($I_2$) is determined at 190° C./2.16 kg, and reported in grams eluted per 10 minutes (g/10 min).

Modulus (Avg-10%), in psi, as stress-strain behavior in uniaxial tension, is determined using ASTM D1708 micro-tensile specimens. The plaques used for microtensile testing were prepared by compression molding using a Tetrahedron press. The polymer was pre-melted at 190° C. for 1 minute at 5 klb, pressed for 5 minutes at 30 klb, and then cooled between cold plates at 17° C. for 1 minute. The gauge length of samples was 22 mm and samples were stretched with an INSTRON at 554% min-1 at 23° C. Tensile strength and elongation at break were reported for an average of 5 specimens. The nominal plaque thickness was 5 mm.

Flexural Modulus (Avg-Flexural Modulus), in ksi, is measured in accordance with ASTM D-790. The plaques used for flexural modulus testing were prepared by compression molding. The composition was pressed under light pressure (6000 psi for 15 minutes), at 130° C., in a Carver press. The press was then opened and closed three times to allow the material to soften and air to escape. The pressure was then increased to 15 tons (30,000 lbs), at which time, the press platens were cooled to a temperature less than 50° C., at a rate of 15° C./minute. Five test bars, each 5 in×0.5 in×0.125 in, were die cut from the compression molded plaques (10 in×7 in×0.120 in). The test involved flexing the bar to failure with a loading nose moving at 0.05 inches/minute, as the bar sat on two radii that were two inches apart, in accordance with ASTM D-790. The data reported herein represents the average flexural modulus of the 5 sample specimens.

Molecular Weight Distribution (MWD), also referred to as a "polydispersity index" (PDI), is defined as the ratio of weight average molecular weight to number average molecular weight ($M_w/M_n$). $M_w$ and $M_n$ are determined according to methods known in the art using conventional gel permeation chromatography (GPC).

Percent (%) Crystallinity. Differential Scanning Calorimetry (DSC) was used to measure percent (%) crystallinity in ethylene-based (PE) polymer samples and propylene-based (PP) polymer samples. About 5 to 8 mg of film sample was weighed and placed in a DSC pan. The film sample was formed by pressing a "0.1 to 0.2 gram" sample at 190° C., 20000 psi, 30 seconds, to form a "1 mil thick" film. The lid was crimped on the pan to ensure a closed atmosphere. The sample pan was placed in a DSC cell, and then heated, at a rate of approximately 10° C./min, to a temperature of 180° C. for PE (230° C. for PP). The sample was kept at this temperature for three minutes. Then the sample was cooled at a rate of 10° C./min to −60° C. for PE (−40° C. for PP), and kept isothermally at that temperature for three minutes. The sample was next heated at a rate of 10° C./min, until complete melting (second heat). The percent crystallinity was calculated by dividing the heat of fusion ($H_f$), determined from the second heat curve, by a theoretical heat of fusion of 292 J/g for PE (165 J/g, for PP), and multiplying this quantity by 100 (for example, % cryst.=($H_f$/292 J/g)× 100 (for PE); and % cryst.=(Hf/165 J/g)×100 (for PP)). Unless otherwise stated, melting point(s) ($T_m$) of each polymer was determined from the second heat curve, and the crystallization temperature ($T_c$) was determined from the first cooling curve.

Scratch Resistance (5-Finger). Five finger scratch mar measurements were carried out according to ASTM Method D7027. It is a mechanically driven apparatus with a movable sledge and five metal fingers—250 mm long. The fingers used in this test method were 1.0±0.1 mm in diameter highly polished steel balls. Each pin was loaded with a different weight exerting standard force (1.38 N, 2.73 N, 5.44 N, 6.78 N, and 11.03 N) on the surface of the test material that was at least 140 mm in length and 10 mm in width. The appropriate weight was added to the top of each finger and weights were aligned according to the pin position and weight. Scratch depth measurements were acquired for each sample specimen at 11.03 N via laser scanning microscopy (LSM). LSM image data was collected using laser scanning microscope equipped with a 408 nm wavelength violet laser. A 20× objective lens was used for image acquisition and six images were stitched together and analyzed. The average of the five scratch depth measurements taken along the profile of scratch area was reported for each sample. Each measurement was taken from a flat area of the sample specimen (see experimental section) to the middle of the scratch. In Table 3, for the ranking (1-5) for the "Scratch Resistance (5-Finger)" test method: for a ranking of 1, scratch mark observed at a force less than, or equal to, 1.38 N; for a ranking of 2, scratch mark observed at a force greater than 1.38 N and less than, or equal to, 2.73 N; for a ranking of 3, scratch mark observed at a force greater than 2.73 N and less than, or equal to, 5.44 N; for a ranking of 4, scratch mark observed at a force greater than 5.44 N and less than, or equal to, 6.78 N; and for a ranking of 5, scratch mark observed at a force greater than 6.78 N and less than, or equal to, 11.03 N.

Comonomer Composition Distribution Breadth (CCDB) is determined according to the following High Temperature Liquid Chromatography (HTLC) method. HTLC is performed according to the methods disclosed in U.S. Pat. Nos. 8,076,147, 8,318,896, and 8,691,916. Samples are analyzed by the following methodology.

A Waters GPCV2000 high temperature SEC chromatograph is reconfigured to build the HT-2DLC instrumentation. Two Shimadzu LC-20AD pumps are connected to the injector valve in GPCV2000 through a binary mixer. The first dimension (D1) HPLC column is connected between the injector and a 10-port switch valve (Valco Inc.). The second dimension (D2) SEC column is connected between the 10-port valve and, an infrared absorbance detector (IR5). The IR5 detector is used for both concentration and composition measurements.). The IR5 detector is provided by PolymerChar, Valencia, Spain.

Columns: The D1 column is a high temperature HYPERCARB graphite column (2.1×100 mm) purchased from Thermo Scientific. The D2 column is a PLRapid-M column purchased from Varian (10×100 mm).

Reagents: HPLC grade trichlorobenzene (TCB) can be obtained from Fisher Scientific. Decane and 2,6-Di-tert-butyl-4-methylphenol (Ionol) can be obtained from Aldrich.

Sample Preparation: 0.2 g of polyolefin sample is placed in a 10-mL Waters autosampler vial. 8-mL of decane with 200 ppm Ionol is added to the vial afterwards. After sparging nitrogen to the sample vial for about 1 min, the sample vial is put on a heated shaker with temperature set at 160° C. The dissolution is done by shaking the vial at the temperature for 2 hr. The vial is then transferred to the autosampler for injection. Please note that the actual volume of the solution may be more than 8 mL due to the thermal expansion of the solvent.

HT-2DLC: The D1 flow rate is set at 0.01 mL/min. The composition of the mobile phase is 100% decane for the first 10 min of the run. The composition is then increased to 60% of TCB in 489 min. The data are collected for 489 min as the duration of the raw chromatogram. The 10-port valve switches every three minutes yielding 489/3=163 SEC chromatograms. A post-run gradient is used after the 489 min data acquisition time to clean and equilibrate the column for the next run:

Clean step:
490 min: flow=0.01 min; //Maintain the constant flow rate of 0.01 mL/min from 0-490 min.
491 min: flow=0.20 min; //Increase the flow rate to 0.20 mL/min.
492 min: % B=100; //Increase the mobile phase composition to 100% TCB
502 min: % B=100; //Wash the column using 2 mL of TCB Equilibrium step: step:
503 min: % B=0; //Change the mobile phase composition to 100% of 1-decanol or decane
513 min: % B=0; //Equilibrate the column using 2 mL of weak eluent
514 min: flow=0.2 mL/min; //Maintain the constant flow of 0.2 mL/min from 491-514 min
515 min: flow=0.01 mL/min; //Lower the flow rate to 0.01 mL/min.

After step 8, the flow rate and mobile phase composition are the same as the initial conditions of the run gradient. step:

The D2 flow rate is at 2.51 mL/min. Two 60 µL loops are installed on the 10-port switch valve. 30-µL of the eluent from D1 column is loaded onto the SEC column with every switch of the valve.

Signals from IR5 detector may be collected by EZChrom (Agilent) through a SS420X analogue-to-digital conversion box and the chromatograms can be exported in ASCII format and imported into a home-written MATLAB software for data reduction. One signal, referred as 'measure' by the manufacturer, is used to determine concentrations of the eluted polymers. The other signal, referred as 'methyl' by the manufacturer, is used to measure concentrations of methyl groups of the eluted polymers. The ratio of methyl to measure (methyl/measure) is used to determine the compositions of the eluted polymers after calibration. Eight polymers with different propylene contents are used in calibration. The polymers are made by metallocene catalyst giving rise to narrow comonomer composition distribution breadth or CCDB. The compositions of the eight polymer standards are determined by NMR as 0, 20.0, 28.0, 50.0, 86.6, 92.0, 95.8, and 100 weight percent of propylene in polymer (wt % P). The calibration curve is constructed by linear fitting of the methyl/measure versus wt % P of these standards. Analysis of the raw data is calculated as follows: the first dimension HPLC chromatogram is reconstructed by plotting the IR signal of every cut (from total IR SEC chromatogram of the cut) as a function of the elution volume. The IR vs. D1 elution volume is normalized by total IR signal to obtain weight fraction vs. D1 elution volume plot. The IR methyl/measure ratio is obtained from the reconstructed IR measure and IR methyl chromatograms. The ratio is converted to composition using the calibration curve of PP wt. % (by NMR) vs. methyl/measure obtained from second dimension SEC experiments.

The CCD breadth of a polymer sample is calculated according to the following equations:

The weight-averaged chemical composition (Wt % P) of polymer fractions eluted at the earliest elution volume ($CC_{HIGH}$):

$$CC_{HIGH} = \frac{\sum_0^{0.25} CC_i W_i}{\sum_0^{0.25} W_i} \quad (1)$$

Where $\Sigma_0^{0.25}$ stands for the sum of the earliest 25% of polymer fractions, $CC_i$ is the chemical composition of fraction i in wt % P, and $W_i$ is the weight fraction of fraction i.

The weight-averaged chemical composition (Wt % P) of polymer fractions eluted at the latest elution volume ($CC_{LOW}$):

$$CC_{LOW} = \frac{\sum_{0.75}^{1} CC_i W_i}{\sum_{0.75}^{1} W_i} \quad (2)$$

Where $\Sigma_{0.75}^{1}$ stands for the sum of the latest 25% of polymer fractions, $CC_i$ is the chemical composition of fraction i in wt % P, and $W_i$ is the weight fraction of fraction i.

The CCDB of a polymer sample is:

$$\text{CCD Breadth} = CC_{HIGH} - CC_{LOW} \quad (3).$$

The unit of CCDB is wt % P.

Reference: D. Lee, M.D. Miller, D.M. Meunier, J. W. Lyons, J.M. Bonner, R.J. Pell, C. Li Pi Shan, T. Hung. Development of high temperature comprehensive two-dimensional liquid chromatography hyphenated with infrared and light scattering detectors for characterization of chemical composition and molecular weight heterogeneities in polyolefin copolymers, J. of Chromatogr. A, 1218 (2011), 7173.

Specific Embodiments

Materials and Reagents
In the Examples detailed below, the following materials are employed:

TABLE 1

| Raw materials | |
|---|---|
| Material | Specification |
| Propylene/ethylene copolymer 1 (PE1) | Propylene/Ethylene copolymer, with density of 0.896-0.897 g/cm$^3$ and melt flow rate MFR of 8.0-12 g/10 min (ave. MFR = 10 g/10 min) (230° C./2.16 kg), MWD = 2.75; 41-42% crystallinity. |
| AFFINITY 1880G | Ethylene/α-Olefin copolymer, with density of 0.904 g/cm$^3$ and melt index $I_2$ of 1.0 g/10 min (190° C./2.16 kg). |
| Filler Masterbatch | 20 wt % AEROSIL R9200 silica particles plus 80 wt % random propylene-based copolymer carrier (density = 0.900 g/cc and MRF = 42 g/10 min). AEROSIL R9200 is a structure modified, hydrophobic fumed silica with specific surface area of 150-190 m$^2$/g (BET) from Evonik Industries AG. |
| VERSIFY 3200 | Propylene/Ethylene copolymer, with density of 0.876 g/cm$^3$ and melt flow rate MFR of 8.0 g/10 min (230° C./2.16 kg), 21% crystallinity. |
| D115A | Polypropylene homopolymer, with density of 0.909 g/cm$^3$ and melt flow rate MFR of 11 g/10 min (230° C./2.16 kg), 61% crystallinity. |
| Braskem 364.01 | Propylene/Ethylene copolymer, with density of 0.900 g/cm$^3$ and melt flow rate MFR of 42 g/10 min (230° C./2.16 kg), 49% crystallinity. |

Synthesis of PE1
A continuous solution polymerization was carried out in a controlled well-mixed reactor. Purified mixed alkanes solvent (ISOPAR E available from Exxon Mobil, Inc.), ethylene, propylene, and hydrogen (where used) were combined, and fed to a 52 gallon reactor. The feeds to the reactor were measured by mass-flow controllers. The temperature of the feed stream was controlled by use of a cooled heat exchanger, before entering the reactor. The catalyst component solutions were metered using pumps and mass flow meters. The reactor was run liquid-full, at approximately 550 psig pressure. Upon exiting the reactor, water and additive were injected into the polymer solution, to terminate remaining polymerization reactions. The solvent and unreacted monomers were removed during a two stage devolatization process of the post reactor, polymer solution process. The polymer melt was pumped to a die for underwater pelletization. See Table 2 below.

TABLE 2

| | Polymerization Conditions for PE1 | | | | | | | | | | | | | |
|---|---|---|---|---|---|---|---|---|---|---|---|---|---|---|
| | C3 Propylene lb/hr | C2 Ethylene lb/hr | Mixed Alkanes Solvent lb/hr | H$_2$ sccm[1] | Temp. ° C. | Cat.[2] Conc. ppm | Cat. Flow lb/hr | Cocat-1[5] Conc. ppm | Cocat 1 Flow lb/hr | Cocat 2[6] Conc. ppm | Cocat 2 Flow lb/hr | Polym Rate[7] lb/hr | Conv[3] wt % | Polymer wt % | Eff.[4] |
| PE1 | 360 | 5.4 | 885 | 800 | 125 | 40 | 0.69 | 400 | 0.60 | 400 | 0.32 | 240 | 66.6 | 19.2 | 8.7 |

[1]Standard cm$^3$/min.
[2]Catalyst: [[2',2'''-[1,2-cyclohexanediylbis(methyleneoxy-κO)]bis[3-(9H-carbazol-9-yl)-5-methyl[1,1'-biphenyl]-2-olato-κO]](2-)]hafnium dimethyl.
[3]Weight percent propylene conversion in reactor.
[4]Efficiency, 1,000,000 lb polymer/lb Hf.
[5]Cocatalyst-1 (Cocat 1): bis-hydrogenated tallow alkyl methylammonium tetrakis-pentafluorophenyl borate (from Boulder Scientific).
[6]Cocatalyst-2 (Cocat 2): modified methaluminoxane (MMAO-3A, from Akzo-Nobel).
[7]Polymerization Rate Study 1

One test example according to the invention, and three comparative examples were prepared according to the formulations provided in Table 3, below.

TABLE 3

Compositions and Properties of Comparative Examples A-C and Inventive Example 1 (wt %)

| Blend Composition (wt %) | Comp. Example A | Comp. Example B | Inventive Example 1 | Comp. Example C |
|---|---|---|---|---|
| Propylene/ethylene copolymer 1 | 100 | — | 95 | 100 |
| AFFINITY 1880G | — | 95 | — | — |
| Filler Masterbatch | — | 5 | 5 | — |
| Cast Film thickness (mil) | | 28 | 28 | 28 |
| Plaque thickness (mil) | 125 | | | |
| Density (g/cc) | 0.897 | 0.908 | 0.903 | 0.897 |
| Scratch Resistance (5-Finger) | 3 | 3 | 5 | 3 |
| Scratch Resistance (scratch depth (μm)) | 2.53 | — | 0.58 | 1.18 |
| Internal Haze (%) | 90 | 17 | 36 | 29 |
| Avg-10% Modulus (psi) | — | 678 | 3906 | 3720 |

Comparative Example A was prepared by injection molding using a Krauss Maffei KM 110-390/390 CL injection molder. Test plaques having dimensions of 16.5 mm×19 mm×3 mm (4 in×6 in×0.125 in) were generated at rates of 150 rpm and temperatures of 200° C. using single molds.

Comparative Examples B and C and Inventive Example 1 were prepared by cast film conditions. Monolayer films having a total thickness of 28±1 mil were prepared using a single 30 mm 25:1 L/D Collin extruder equipped with two knife trim station and chill rollers. Screw speeds of 75 rpm, maximum heating temperatures of 230° C. and chill roll temperatures of 22° C. were utilized.

The samples were examined for density, scratch resistance (5-Finger), internal haze, average 10% modulus and average flexural modulus, according to the test methods described herein.

Summary of Results. It has been discovered that the inventive compositions have a good balance of scratch resistance and internal haze. Inventive Example 1 showed an overall better balance of scratch resistance and internal haze, as compared to Comparative Examples A to C. In regard to the cast films, Inventive Example 1 clearly had improved scratch resistance, as shown by a lower scratch depth as compared to Comparative Examples B and C. In regard to the plaque of Comparative Example A, the Inventive Example 1 also showed improved scratch resistance, as shown the lower scratch depth. Inventive Example 1 showed a 77% reduction in scratch depth. Since the scratch resistance is a surface property feature, one would expect that the thickness of the sample would not affect the scratch depth to such an extent (77% reduction) as seen in Example 1. Inventive Example 1 still maintained good (low) internal haze.

Study 2

In this study, each example was prepared by injection molding using a Krauss Maffei KM 110-390/390 CL injection molder, as discussed above. The samples were examined for density, scratch resistance (5-Finger), internal haze, average 10% modulus and average flexural modulus, and percent (%) crystallinity, according to the test methods described herein. Results are shown in Table 4 below.

TABLE 4

Compositions and Properties of Comp. Examples D and E and Inv. Examples 2 and 3 (wt %)

| | Inv. 2 | Comp. D | Inv. 3 | Comp. E |
|---|---|---|---|---|
| PE1 (41-42% cryst, 10 MFR) | 95 | | | 34.5 |
| VERSIFY 3200 (21% cryst, 8 MFR) | | 95 | | |
| D115A (11 MFR hPP; 61% crystallinity) | | | 95 | |
| Braskem 364.01 (49% cryst., 42 MFR) | | | | 60.5 |
| Filler Masterbatch | 5 | 5 | 5 | 5 |
| Total | 100 | 100 | 100 | 100 |
| Fabrication Process | Injection molding | Injection molding | Injection molding | Injection molding |
| Plaque thickness (mil) | 125 | 125 | 125 | 125 |
| Density (g/cc) | 0.903 | 0.884 | 0.915 | 0.906 |
| Scratch Resistance (5-Finger) | 5 | 2 | 4 | 4 |
| Scratch Resistance (scratch depth (μm)) | 0.74 | 10.53 | 0.82 | 1.03 |
| Internal Haze (%) | 89 | 66 | 98 | 44 |
| Avg-10% Modulus (psi) | 3748 | 942 | 5347 | 3955 |
| Crystallinity composition (%) | 43.2 | 23.1 | 62.4 | 47.6 |

Summary of Results. It has been discovered that the Inventive Example 2 showed an overall better balance of high scratch resistance and low internal haze, as compared to Comparative Example D and Inventive Example 3, which each contained a propylene-based polymer with a percent crystallinity outside of a preferred range of 25 to 60%. Inventive Example 2 also showed an overall better balance of high scratch resistance and low internal haze, as compared to Comparative Examples E, which contained a majority amount of a propylene-based polymer with a melt flow rate (MFR) greater than 30 g/10 min.

Study 3—Multi-Layered Tile

A Luxury Vinyl Tile (LVT) is made using one of more vinyl layers (often filled) as a base. A décor film layer also made of vinyl is then laminated to that base. The décor film layer is then covered by a vinyl "wear" layer that is typically laminated on top. Often a UV resin top coat is added for extra protection. There is a need for vinyl-free alternatives, for example, the use of one or more olefin-based polymers in the backing layer and the wear layer. Propylene-ethylene copolymers provide a balance of hardness and contact clarity. However, all of the layers of the tile must to adhere well together. An extrusion coating approach to the formation of such a tile would provide improved adhesion and be cost effective to manufacture the tile. A tandem extrusion coating setup can be used to efficiently produce the entire tile on one continuous process, as opposed to the multiple steps required for construction by lamination. The various layers are described below.

Base Layer. A first Extruder 1 can be used to extrude a filled backing layer as the base layer, e.g., made of an olefin-based polymer, such as an ENGAGE Polyolefin Elastomer, a PRIMACOR Elastomer, or an INFUSE Olefin Block Copolymer, available from The Dow Chemical Company. Use of such polymers allows for a tunable flexibility of the base layer, and therefore the entire structure, by modifying the comonomer and comonomer content of the olefin-based polymer to adjust the resulting density and flexibility. Large amounts of fillers, such as calcium carbonate, coal fly ash, and the like, can be added to levels up to 80 wt %, based on the weight of the base layer.

Décor Layer. The décor layer is used to give the finished product a look of a material, such as, for example, wood or marble. This film can also be made of an olefin-based polymer to allow for an all-olefin polymer and readily recyclable structure. A propylene-based polymer or an ethylene-based polymer can be used to make the base film, upon which a pattern can be printed. Such a film can be designed so as not to shrink upon seeing heat from other layers during construction. Propylene-based polymers are preferred due to their higher melting points. A layer of an adhesive primer can be added to the decorative side (the printing itself) of the décor layer to protect the design and to allow for easier adhesion to the wear layer.

Wear Layer. In embodiments, the wear layer can be made of either an ethylene-based polymer or a propylene-based polymer, with a propylene-based polymer being preferred, due to its higher crystallinity and melting point. A propylene-based polymer would also be expected to give better abrasion and mar characteristics. This layer should have reasonable contact clarity such that the décor can be seen through it. This layer can also be extruded with a single screw extruder.

Top Coat. The top coat is an extra-finish coating layer that provides enhanced abrasion and mar characteristics, and also controls the gloss of the finished product. Typical top coatings are UV curable polyurethanes and acrylics.

Figure 2:
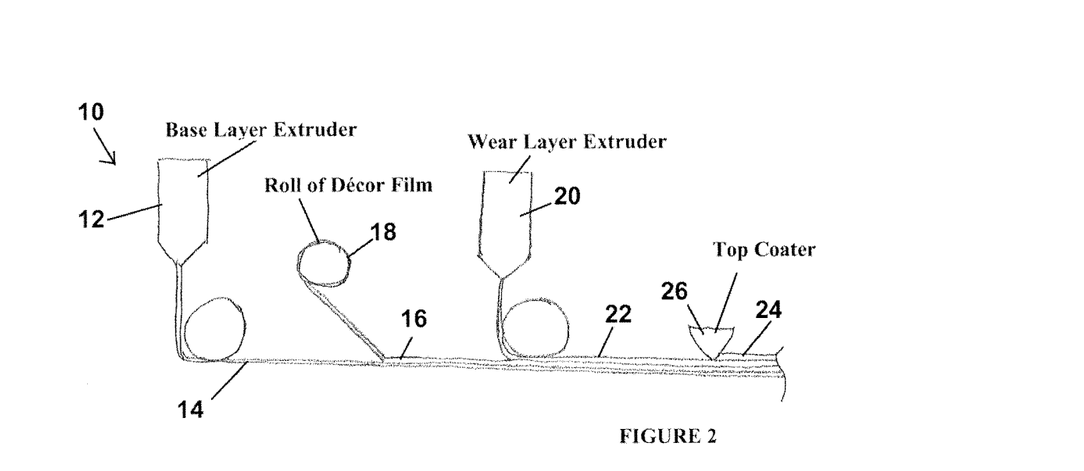
FIG. 2 depicts a tandem extrusion coating process to form a multi-layer tile.

Process to Make an All-Olefin Tile. FIG. 2 depicts an example of a representative tandem extrusion coating process, designated generally by the numeral 10, to form an all-olefin polymer, multi-layer tile. In preferred embodiments, the process is continuous. As depicted in FIG. 2, a filled backing layer can be extruded from a first extruder/die setup 12, into a flexible (or semi-rigid) backing film or sheet (base layer) 14. While still hot, a pre-fabricated décor film 16 can be fed from a roll 18, held in place on a standard unwind stand, onto the base layer 14. A second extruder/die setup 20 can then lay a molten wear layer 22 down onto the top of the décor film 16. After ambient cooling, and the optional application of cooling rolls (not shown), a top coat 24 can be applied onto the wear layer 22 at standard coating station 26.

It is specifically intended that the present invention not be limited to the embodiments and illustrations contained herein, but include modified forms of those embodiments, including portions of the embodiments and combinations of elements of different embodiments, as come within the scope of the following claims.

We claim:

1. A composition comprising at least the following:
    A) at least 50 wt %, based on the total weight of the composition, of a propylene-based polymer that has a % crystallinity as determined by differential scanning calorimetry (DSC) of greater than, or equal to, 25%, a MFR from 0.5 to 30.0 g/10 min (230° C./2.16 kg), a molecular weight distribution (Mw/Mn) of 1.5 to 5, and a density of 0.888g/cc to 0.910 g/cc; and
    B) from 0.5 to 10.0 wt % of a filler, based on the total weight of the composition.

2. The composition of claim 1, wherein the propylene-based polymer (Component A) has a % crystallinity from 25% to 60%.

3. The composition of claim 1, wherein the propylene-based polymer (Component A) is a propylene/ethylene copolymer.

4. The composition of claim 1, wherein the weight ratio of the propylene-based polymer (Component A) to the filler (Component B) is greater than 20.

5. The composition of claim 1, wherein the combined weight of Components A and B is ≥95 wt %, based on the total weight of the composition.

6. A crosslinked composition formed from the composition of claim 1.

7. An article comprising at least one component formed from the composition of claim 1.

8. A composition comprising at least the following:
    A) from 80 to 99.5 wt %, based on the total weight of the composition, of a propylene-based polymer that has a % crystallinity as determined by differential scanning calorimetry (DSC) of greater than, or equal to, 25%, and a MFR from 0.5 to 30.0 g/10 min (230° C./2.16 kg); and
    B) from 0.5 to 10.0 wt % of a filler, based on the total weight of the composition.

9. The composition of claim 8, wherein the propylene-based polymer (Component A) has a % crystallinity from 25% to 60%.

10. The composition of claim 8, wherein the propylene-based polymer (Component A) has a molecular weight distribution (Mw/Mn) of 1.5 to 5, a density of 0.888 g/cc to 0.910 g/cc.

11. The composition of claim 8 having a melt flow rate (MFR) of 1 to 15g/10 min. (230° C./2 kg), a density of 0.888 to 0.950 g/cm³.

12. A crosslinked composition formed from the composition of claim 8.

13. A composition comprising at least the following:
    A) at least 50 wt %, based on the total weight of the composition, of a propylene-based polymer that has a % crystallinity as determined by differential scanning calorimetry (DSC) of greater than, or equal to, 25%, and a MFR from 0.5 to 30.0 g/10 min (230° C./2.16 kg); and
    B) from 0.5 to 10.0 wt % of a filler, based on the total weight of the composition,
    wherein the composition has a melt flow rate (MFR) of 1 to 15 g/10 min. (230° C./2 kg), a density of 0.888 to 0.950 g/cm³.

14. The composition of claim 13 comprising 80 to 99.5 wt % of the propylene-based polymer (Component A).

15. The composition of claim 13 wherein the propylene-based polymer (Component A) has a molecular weight distribution (Mw/Mn) of 1.5 to 5, a density of 0.888 g/cc to 0.910 g/cc.

16. The composition of claim 13, wherein the propylene-based polymer (Component A) has a % crystallinity from 25% to 60%.

17. A crosslinked composition formed from the composition of claim 13.

* * * * *